United States Patent
Richter et al.

(10) Patent No.: US 6,822,122 B2
(45) Date of Patent: Nov. 23, 2004

(54) METHOD FOR THE HYDROFORMYLATION OF OLEFINS COMPRISING 2 TO 8 CARBONS ATOMS

(75) Inventors: Wolfgang Richter, Wachenheim (DE); Roland Krokoszinski, Weisenheim a.Berg (DE); Rolf Müller, Dannstadt-Schauernheim (DE); Michael McAtee, Chesapeake, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/311,371

(22) PCT Filed: Jun. 27, 2001

(86) PCT No.: PCT/EP01/07336

§ 371 (c)(1),
(2), (4) Date: Dec. 16, 2002

(87) PCT Pub. No.: WO02/00582

PCT Pub. Date: Jan. 3, 2002

(65) Prior Publication Data

US 2003/0153791 A1 Aug. 14, 2003

(30) Foreign Application Priority Data

Jun. 28, 2000 (DE) .......................................... 100 31 520

(51) Int. Cl.[7] .............................................. C07C 45/29
(52) U.S. Cl. ....................................... 568/451; 568/454
(58) Field of Search .................................. 568/451, 454

(56) References Cited

U.S. PATENT DOCUMENTS

| 4,827,043 A | 5/1989 | Butler ......................... 568/492 |
|---|---|---|
| 5,648,553 A | 7/1997 | Ueda et al. .................. 568/454 |
| 6,100,423 A | 8/2000 | Borgell et al. ............... 568/454 |
| 2004/0015011 A1 | 1/2004 | Krokoszinski et al. ....... 562/521 |
| 2004/0024259 A1 | 2/2004 | Richter et al. .............. 568/451 |

FOREIGN PATENT DOCUMENTS

| JP | 08092146 | 4/1996 |
| JP | 08208552 | 8/1996 |

OTHER PUBLICATIONS

Walz et al., U.S. Ser. No. 10/312,360 corresponding to US 2003/176743 A1 (filing date: Dec. 26, 2002).

M. Beller et al. "Today's oxo processes" Jnl. of Molecular Catalysts A: vol. 104 (1995) pp. 46–48.

*Primary Examiner*—Johann Richter
*Assistant Examiner*—Sikarl A. Witherspoon
(74) *Attorney, Agent, or Firm*—Keil & Weinkauf

(57) ABSTRACT

Disclosed is a method for the hydroformylation of olefins comprising 2 to 8 atoms, whereby a) an inflow containing olefins and a gas mixture containing hydrogen and carbon monoxide are fed into a reaction zone and reacted in the presence of a hydroformylation catalyst, b) the reaction product which is released from the raw hydroformylation product is redirected into the reaction zone during the extraction of a gaseous recovery flow. The inventive method is characterised in that c) the recovery flow is brought into intimate contact with a wash liquid in order to eliminate the unreacted olefins contained therein, the wash liquid being a vented hydroformylation product, and the olefin-charged wash liquid and the raw hydroformylation product are redirected for regeneration. Said inventive method enables unreacted olefins to be reclaimed to a large extent from the recovery flow.

10 Claims, 3 Drawing Sheets

METHOD FOR THE HYDROFORMYLATION OF OLEFINS COMPRISING 2 TO 8 CARBONS ATOMS

Figure 1:
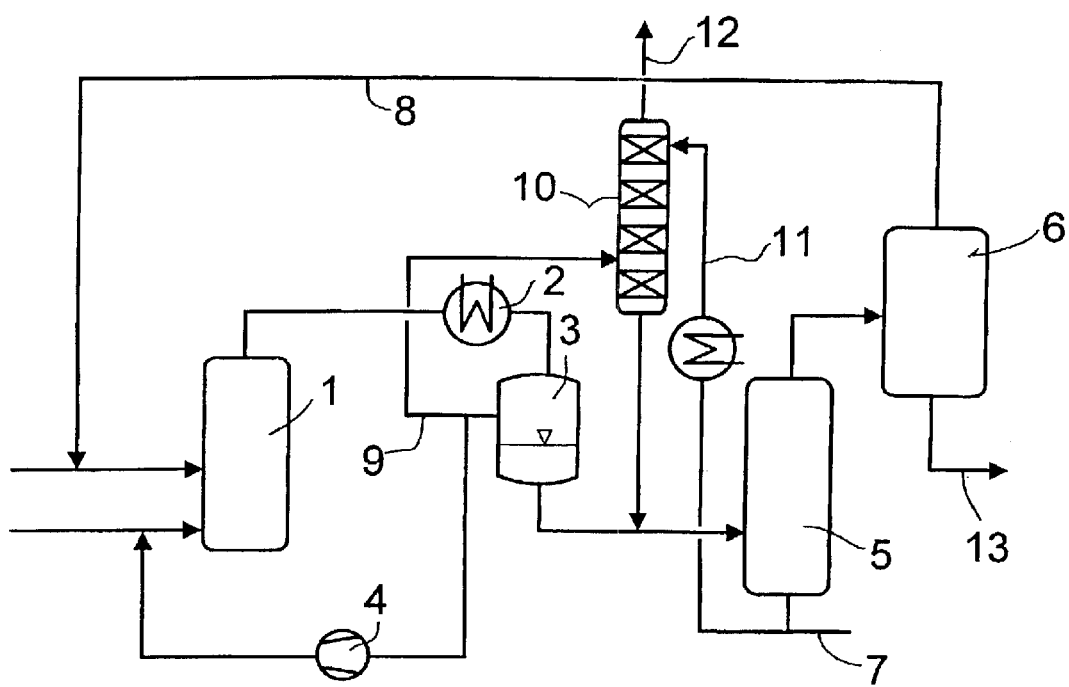

The present invention relates to a process for the hydroformylation of olefins having from 2 to 8 carbon atoms.

Hydroformylation or the oxo process is an important industrial process and is employed for preparing aldehydes from olefins and synthesis gas, i.e. a mixture of carbon monoxide and hydrogen. Hydroformylation is carried out in the presence of catalysts which are homogeneously dissolved in the reaction medium. Catalysts used are generally compounds or complexes of metals of transition group VIII, usually Co or Rh compounds or complexes which may be unmodified or modified with, for example, amine- or phosphine-containing compounds.

In the hydroformylation of lower olefins, virtually complete conversion of the olefin used can be achieved only when there is a sufficiently large reaction space in the hydroformylation reactor. In order to achieve an acceptable space-time yield, the reaction is generally carried out to only partial conversion based on the olefin used. The hydroformylation product is separated off from the output stream from the reactor and the remaining constituents of the output stream are recirculated to the hydroformylation reactor together with fresh carbon monoxide and hydrogen. However, the gaseous inert components, i.e. gases which do not react in the hydroformylation, for example nitrogen, methane, argon, etc., which have been introduced with the synthesis gas and/or olefin are also returned to the reactor together with the recycle stream. To prevent the concentration of the inert components from rising continually in the hydroformylation reactor and reaching values at which the hydroformylation reaction ceases, a substream of the recycled stream or part of the gas phase in the hydroformylation reactor has to be bled from the process in order to remove the inert components introduced with the synthesis gas and/or the olefin-containing feed from the system.

M. Beller et al., Journal of Molecular Catalysis A: 104 (1995), 46–48 and the accompanying FIG. 3, describe a typical gas recycle process for the hydroformylation of lower olefins. Carefully purified propylene and synthesis gas (1,2) are introduced together with circulating gas into the reactor (3). The gaseous output from the reactor passes through a demister (4) for precipitating entrained droplets of liquid products. The gaseous hydroformylation product is condensed in a condenser (5) and collected in a separation vessel (6) from which the circulating gas is taken off via a demister (7) and a compressor (8) and recirculated to the reactor (3). A substream or bleed stream (vent) is discharged. The crude hydroformylation product from the separation vessel (6) is passed to work-up.

The bleed stream comprises not only the inert components but also considerable amounts of unreacted olefin and other components of value, which are thus lost to the reaction. To keep the bleed stream and the olefin losses associated therewith small, use is generally made of a synthesis gas of high purity. However, this pure synthesis gas is significantly more expensive than synthesis gases of lower purity. Synthesis gases of lower purity, i.e. those having a high content of inert components, cannot be used in industrial hydroformylation processes without special measures for the abovementioned reasons. To prevent the concentration of inert components in the hydroformylation reactor reaching unacceptable levels, the bleed stream would have to be so large that the accompanying loss of unreacted olefin would cancel out the savings made by using the cheaper feed stock.

JP 08092146-A describes a process for the hydroformylation of $C_2$–$C_6$-olefins. The waste gas obtained in the distillation to separate off the catalyst is compressed in order to liquefy the aldehyde present therein.

JP 08208552-A describes a hydroformylation process in which the waste gas streams obtained are subjected to scrubbing with the high-boiling by-products of the hydroformylation to recover the products of value present therein.

It is an object of the present invention to provide a process for the hydroformylation of lower olefins which allows the use of synthesis gas in which inert gas is present, without significant amounts of starting materials being lost via the bleed stream.

We have found that this object is achieved by a process for the hydroformylation of olefins having from 2 to 8 carbon atoms, in which a) an olefin-containing feed and a gas mixture comprising hydrogen and carbon monoxide are fed into a reaction zone and reacted in the presence of a hydroformylation catalyst, homogeneously dissolved in the reaction medium, b) the crude hydroformylation product is separated from the output stream from the reaction zone, a gaseous bleed stream is discharged and the remainder of the output stream is recirculated to the reaction zone, wherein c) the bleed stream is brought into intimate contact with a scrubbing liquid to remove unreacted olefins present in the bleed stream, where the scrubbing liquid is degassed hydroformylation product, and the olefin-laden scrubbing liquid together with the crude hydroformylation product is passed to work-up.

The gaseous bleed stream can be taken off at any point on the circuit comprising hydroformylation reactor, separation of crude hydroformylation product and recirculation of the reactor output which has been freed of the hydroformylation product. The bleed stream can, for example, be taken from the gas phase of the reaction zone. Part of the recirculated reactor output which has been freed of hydroformylation product is branched off and discharged as bleed stream.

The size of the bleed stream is generally calculated so that, averaged over time, all gaseous inert components such as nitrogen, methane, argon, etc., introduced with the olefin-containing feed and the synthesis gas are removed from the system.

The bleed stream comprises, before it is brought into contact with the scrubbing liquid, variable amounts of unreacted olefin, hydroformylation product, saturated hydrocarbons (in particular the alkane corresponding to the olefin used) and gaseous inert components such as nitrogen, methane and argon, etc., depending on the point at which it is taken off.

The gaseous bleed stream is, before it is discharged from the process, brought into intimate contact with a scrubbing liquid to remove unreacted olefins and any other products of value, such as hydroformylation products or alkanes present in the bleed stream. According to the present invention, the scrubbing liquid used is degassed hydroformylation product, preferably the hydroformylation product which has been obtained in the work-up of the output from the reactor and has been largely freed of unreacted olefins, i.e. the alkanal and/or alkanol having one more carbon atom than the olefin reacted. For the present purposes, "degassed" means that the hydroformylation product can take up, i.e. dissolved, olefins under the pressure and temperature conditions under which it is brought into contact with the bleed stream. In other words, "degassed" is intended to mean that the alkanal and/or alkanol used as scrubbing liquid is not saturated with olefin. The scrubbing liquid laden with the olefins (and any other products of value) is then passed to the work-up section of the process of the present invention.

The scrubbing liquid can be brought into contact with the gaseous bleed stream in any apparatus suitable for scrubbing a gas by means of a liquid. The gas and liquid are advantageously brought into contact in a column in which the bleed stream is introduced into the bottom or the lower part of the column and the scrubbing liquid is introduced at the top or in the upper part of the column and is passed through the column in countercurrent to the bleed stream. To create a large surface area, the column is preferably provided with internals such as trickle trays or packing such as Raschig rings, spirals or saddles, or other internals. The gas and liquid are brought into contact according to the countercurrent principle, with the laden scrubbing liquid being taken off in the lower part of the column and the purified bleed stream being taken off in the upper part of the column.

The bleed stream and scrubbing liquid are preferably brought into contact under conditions under which essentially complete transfer of the unreacted olefin present in the bleed stream and any further products of value present to the scrubbing liquid is possible. The absorption of the unreacted olefin and possibly further components of the bleed stream in the scrubbing liquid liberates heat of solution which leads to an increase in the temperature of the scrubbing liquid. Owing to the decreasing solubility of gases in liquids as the temperature increases, the absorption capacity of the scrubbing liquid decreases with increasing temperature. For this reason, the scrubbing liquid is preferably cooled to below 50° C., in particular below 40° C., before it is brought into contact with the bleed stream. Furthermore, when using a column for bringing scrubbing liquid and bleed stream into contact, preference is given to actively cooling the column and/or the scrubbing liquid conveyed in countercurrent to the bleed stream. This can be achieved, for example, using heat exchangers installed in the column so that the scrubbing liquid has to flow down over them. Another possible method of cooling is to collect the scrubbing liquid at one or more points in the column and conveying it by means of a pump through an external heat exchanger and subsequently back into the column. In general, the scrubbing liquid and bleed stream are brought into contact at from 20 to 50° C., preferably from 25 to 45° C.

The relative amount of scrubbing liquid which is brought into contact with the bleed stream is preferably such that virtually complete transfer of the products of value into the scrubbing liquid occurs at the temperature at which the gas and liquid are brought into contact. After the laden scrubbing liquid has been separated off, the bleed stream may still contain components of value depending on the vapor pressures of the unreacted olefin, the saturated hydrocarbons or the hydroformylation product. It may therefore be advantageous to cool, e.g. by means of an after-cooler, and/or to compress the bleed stream which has been separated from the scrubbing liquid until the olefin and/or hydroformylation product present in the bleed stream condense. The condensed olefin and/or hydroformylation product can be collected and returned to the process.

The bleed stream which has been treated with the scrubbing liquid comprises not only inert gases but also significant amounts, typically from 30 to 70% by weight, of carbon monoxide and hydrogen. It can, for example, be used to generate heat or be employed as starting material for processes which use hydrogen and place no particular demands on its purity. Thus, for example, the stream is suitable for the preparation of methanol. An overview of customary processes for preparing methanol from $CO/H_2$-containing gases may be found in K. Weissermel and H. -J. Arpe, "Industrielle organische Chemie", VCH, 4th Edition, 1994, p. 31 ff.

Olefins which can be hydroformylated by the process of the present invention contain from 2 to 8 carbon atoms. They can be straight-chain, branched or cyclic olefins. Preferred examples of suitable olefins are ethene, propene, 1-butene and 2-butene. One or more olefins may be present in the olefin-containing feed. The process of the present invention is particularly suitable for use of propylene to produce n-butanal and isobutanal. However, the use of ethylene to produce propionaldehyde or of 1-butene to produce n-valeraldehyde and isovaleraldehyde is also possible. The olefin-containing feed used may further comprise a proportion of a saturated hydrocarbon, in general a saturated hydrocarbon having the same number of carbon atoms as the olefin used. In the treatment of the bleed stream with the scrubbing liquid according to the present invention, most of the saturated hydrocarbon is transferred together with the unreacted olefin to the scrubbing liquid and can in this way be recirculated to the process. To prevent a continuous rise in the concentration of the saturated hydrocarbon in the reaction zone, it is generally necessary to provide for the saturated hydrocarbon to be separated off at some point in the process. The mixture of unreacted olefin and saturated hydrocarbon obtained in the degassing of the crude hydroformylation product can advantageously be separated, e.g. by distillation, into an olefin-enriched fraction and an olefin-depleted fraction, with only the olefin-enriched fraction being returned to the reaction zone.

The gas mixture comprising hydrogen and carbon monoxide which is used is usually referred to as synthesis gas. The composition of the synthesis gas can vary within wide limits. The molar ratio of carbon monoxide to hydrogen is generally from 2:1 to 1:2, in particular from 45:55 to 50:50. The process of the present invention is particularly advantageous when the synthesis gas further comprises inert gases such as nitrogen, methane or argon, e.g. in an amount of from 1 to 15% by volume.

The temperature in the hydroformylation reaction is generally in a range from 50 to 200° C., preferably from about 60 to 190° C., in particular from about 90 to 190° C. The reaction is preferably carried out at a pressure in the range from about 10 to 700 bar, preferably from 15 to 200 bar, in particular from 15 to 60 bar. The reaction pressure can be varied as a function of the activity of the hydroformylation catalyst used.

Only partial conversion, based on the olefin fed in, takes place per pass through the reaction zone. The conversion is generally from 10 to 90%, based on the olefin fed in.

The separation of the crude hydroformylation product from the output from the reaction zone can be carried out in various ways. One method is to use the liquid output process in which the output from the hydroformylation reactor, which is essentially liquid except for the synthesis gas used in excess for the hydroformylation and gaseous inert components, is depressurized in a depressurization vessel in which the output stream is, as a result of the pressure decrease, separated into a liquid phase comprising the catalyst, high-boiling by-products and small amounts of hydroformylation product and unreacted olefin and a gas phase comprising the excess synthesis gas together with the major part of the hydroformylation product formed and the unreacted olefin and also the inert components. The liquid phase can be recirculated as recycle stream to the reaction zone in order to recycle the catalyst. The gas phase is taken off and, for example, passed to a condenser in which the crude hydroformylation product is separated out in liquid form. The gas phase obtained in the condenser, which comprises essentially an unreacted synthesis gas and unreacted olefin together with inert components is wholly or partly recirculated to the reaction zone.

The gas and liquid phases obtained in the depressurization step can advantageously be worked up by the method described in WO 97/07086. For this purpose, the liquid phase is heated and introduced into the upper region of a column, while the gas phase is introduced into the bottom of the column. Liquid phase and gas phase are thereby conveyed in countercurrent. To increase the contact of the phases with one another, the column is preferably provided with packing. As a result of the intimate contact of the gas phase with the liquid phase, the residual amounts of hydroformylation product and unreacted olefin present in the liquid phase are transferred to the gas phase, so that the gas stream leaving the column at the top is enriched in hydroformylation product and unreacted olefin compared to the gas stream introduced at the lower end of the column. The further work-up of the gas stream leaving the column and of the liquid phase leaving the column is carried out in a customary manner, for example as described above.

Alternatively, it is possible to employ the gas recycle process in which a gas stream is taken from the gas space of the reaction zone. This gas stream consists essentially of synthesis gas, unreacted olefins and inert components together with an amount depending on the vapor pressure of the hydroformylation product in the reaction zone of the hydroformylation product formed in the hydroformylation reaction. The hydroformylation product present in the gas stream is condensed out from the gas stream, e.g. by cooling, and the gas stream which has been freed of the liquid fraction is recirculated to the reaction zone.

The crude hydroformylation product is worked up by customary methods. The crude hydroformylation product generally comprises significant amounts of dissolved unreacted olefin and possibly saturated hydrocarbons. For this reason, the crude hydroformylation product is preferably degassed in a first work-up step. The degassed hydroformylation product obtained in this way is suitable as scrubbing liquid in the process of the present invention. To degas the crude hydroformylation product, it can be depressurized, heated and/or treated with a stripping gas such as synthesis gas or nitrogen. Degassing is advantageously carried out in a heated column into which the crude hydroformylation product is fed in the middle region of the column and the degassed hydroformylation product is taken off from the bottom of the column. A gas stream consisting essentially of unreacted olefin or of a mixture of unreacted olefin and saturated hydrocarbon is obtained at the top of the column. This gas stream can be separated into its constituents, namely olefin and saturated hydrocarbon. The olefin obtained at the top of the column or after fractionation of the mixture obtained is advantageously returned to the reaction zone.

Suitable hydroformylation catalysts are the customary transition metal compounds and complexes known to those skilled in the art, which may be used with or without cocatalysts. The transition metal is preferably a metal of transition group VIII of the Periodic Table, in particular Co, Ru, Rh, Pd, Pt, Os or Ir, especially, Rh, Co, Ir or Ru.

Suitable catalysts are, for example, rhodium complexes of the formula $RhX_mL^1L^2(L^3)_n$, where X is a halide, preferably chloride or bromide, alkylcarboxylate or arylcarboxylate, acetylacetonate, arylsulfonate or alkylsulfonate, in particular phenylsulfonate and toluenesulfonate, hydride or the diphenyltriazine anion, $L^1, L^2, L^3$ are, independently of one another, CO, olefins, cycloolefins, preferably cyclooctadiene (COD), dibenzophosphole, benzonitrile, $PR_3$ or $R_2P—A—PR_2$, m is 1 or 3 and n is 0, 1 or 2. R (the radicals R may be identical or different) are alkyl, cycloalkyl and aryl radicals, preferably phenyl, p-tolyl, m-tolyl, p-ethylphenyl, p-cumyl, p-t-butylphenyl, p-$C_1$–$C_4$-alkoxyphenyl, more preferably p-anisyl, xylyl, mesityl, p-hydroxyphenyl which may also be in ethoxylated from, isopropyl, $C_1$–$C_4$-alkoxy, cyclopentyl or cyclohexyl. A is 1,2-ethylene or 1,3-propylene.

$L^1, L^2$ and $L^3$ are preferably, independently of one another, CO, COD, $P(phenyl)_3$, $P(i-propyl)_3$, $P(anisyl)_3$, $P(OC_2H_5)_3$, $P(cyclohexyl)_3$, dibenzophosphole or benzonitrile.

X is preferably hydride, chloride, bromide, acetate, tosylate, acetylacetonate or the diphenyltriazine anion, in particular hydride, chloride or acetate.

Particularly preferred hydroformylation catalysts are phosphorus-containing rhodium catalysts such as $RhH(CO)_2(PPh_3)_2$ or $RhH(CO)(PPh_3)_3$.

Suitable hydroformylation catalysts are described, for example, in Beller et al., Journal of Molecular Catalysis A: 104 (1995), pp. 17–85, which is hereby fully incorporated by reference.

The invention has the following advantages: the unreacted olefin and the hydroformylation product present in the bleed stream are separated off from the bleed stream and are returned to the process. This makes it unnecessary to keep the bleed stream as small as possible. It is therefore possible to use a synthesis gas having a significantly higher content of inert components such as methane, nitrogen, argon, etc., which is significantly cheaper to purchase. Furthermore, the process of the present invention makes it possible to carry out the hydroformylation at a higher olefin partial pressure in the reaction zone. A partial pressure of the olefin corresponding to from 30 to 40% of the total pressure can advantageously be set, particularly in the case of propylene. Under otherwise identical conditions, the higher olefin partial pressure in the reaction zone leads to a higher hydroformylation reaction rate. Alternatively, the same reaction rate can be achieved at a lower concentration of the hydroformylation catalyst. This effect can advantageously be exploited in the case of ligand-modified rhodium catalysts. It has surprisingly been found that the stability of the rhodium catalyst is higher at lower concentration than at high catalyst concentrations. The deactivation of the active complex by ligand degradation proceeds significantly more slowly at low concentrations. Suitable rhodium catalyst concentrations are, for example, from 50 to 250 ppm of rhodium, based on the liquid phase in the reaction zone.

Figure 2:
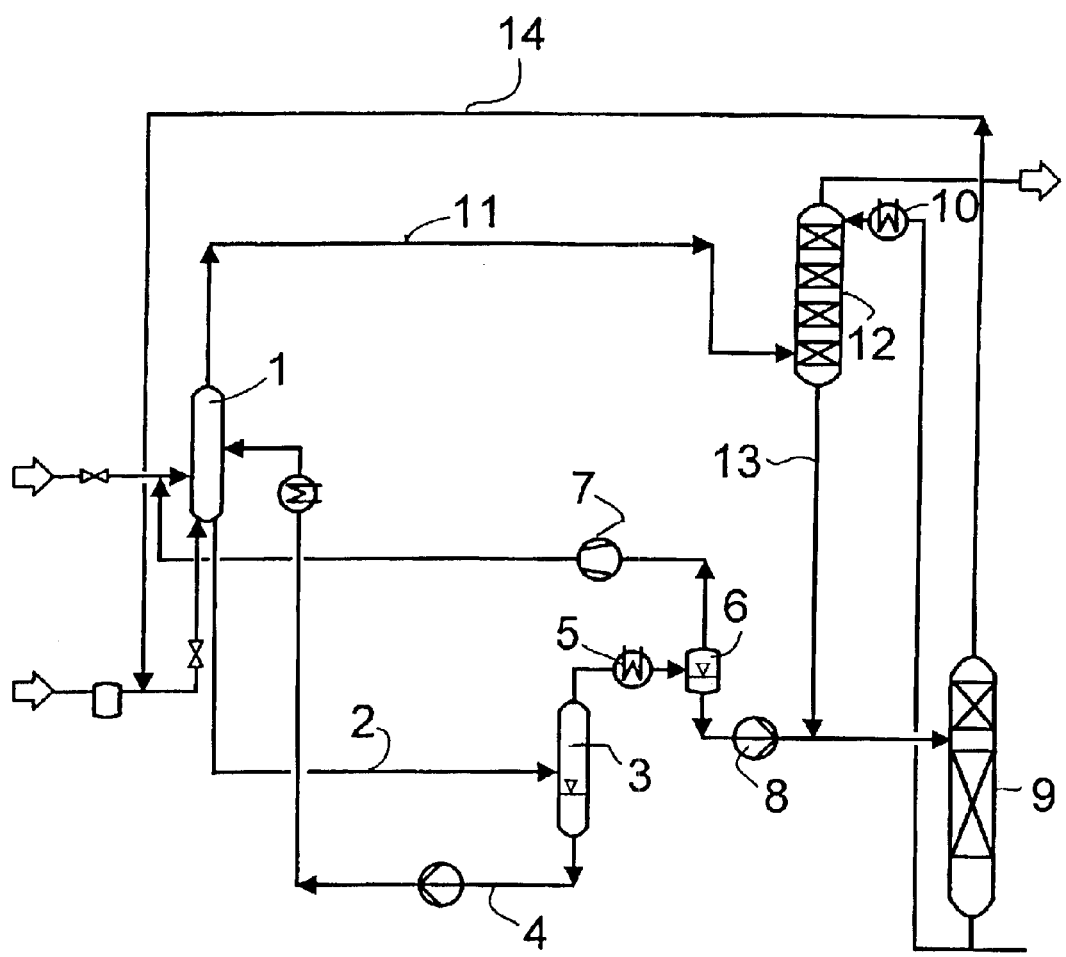

Advantageous embodiments of the process of the present invention are depicted in FIG. 1 and FIG. 2 and are described below. Self-evident plant details which are not necessary to illustrate the process of the present invention have been left out for reasons of clarity.

FIG. 1 schematically shows the process of the present invention carried out using the gas recycle method FIG. 2 schematically shows the process of the present invention with liquid output.

In the embodiment shown in FIG. 1, an olefin-containing feed comprising the olefin to be hydroformylated and a saturated hydrocarbon and an olefin-containing stream recirculated via line (8) and also synthesis gas are fed into the reactor (1) and hydroformylated to partial conversion there. A gaseous stream comprising unreacted olefin, saturated hydrocarbon, unreacted synthesis gas and a hydroformylation product is taken from the gas space of the reactor. This stream is cooled in the heat exchanger (2) and fed into a phase separation vessel (3). Part of the gaseous fraction is recirculated to the reactor (1) via the pressure pump (4). The liquid fraction obtained in the separation vessel (3), which consists essentially of crude hydroformylation product together with olefin and saturated hydrocarbon dissolved therein, is fed to the degassing column (5) at the top of which a mixture of olefin and saturated hydrocarbon is obtained. This mixture can be separated in a rectification column (6) into an olefin-enriched stream which is recirculated to the reactor (1) via line (8) and an olefin-depleted stream (13) which is discharged from the process. The crude hydroformylation product is taken off at the bottom of the degassing column (5) and is subsequently worked up further. A bleed stream via which the inert gases are discharged is taken via line (9) from the circulating gas system. The bleed stream is introduced into the lower part of the column (10) where it rises in the interior of the column. At the top of the column, degassed hydroformylation product from the bottom of the degassing column (5) is introduced via line (11) and passed through the column in countercurrent to the ascending bleed stream. The unreacted olefin present in the bleed stream and a major part of the hydroformylation product are thereby scrubbed out and are conveyed together with the bottoms from the column (10) back to the degassing column (5). To improve the uptake capacity of the scrubbing liquid, the heat of absorption can be removed by means of heat exchangers (not shown) provided on column (10) and the temperature can thus be kept, for example, below 50° C. The waste gas leaving the column (10) via line (12) can be cooled to, for example, 0° C. to condense residual amounts of olefin and hydroformylation product. The condensate can be separated off and combined with the bottoms from the column (10).

In the embodiment shown in FIG. 2, the olefin to be hydroformylated and synthesis gas are fed into the reactor (1) and reacted there. The output from the hydroformylation is depressurized via line (2) into the depressurization vessel (3), where a liquid phase and a gas phase are formed as a result of the pressure decrease and vaporization of low boiling components. The liquid phase separated out in the depressurization vessel (3) is taken off as a liquid stream via line (4) and recirculated to the hydroformylation reactor. The gas stream taken off from the gas space of the depressurization vessel (3), which is enriched in the hydroformylation product and unreacted olefin and further comprises inert components and saturated hydrocarbons as well as unreacted synthesis gas is passed to a condenser (5) in which relatively high-boiling constituents, essentially the hydroformylation product and part of the unreacted olefin and the saturated hydrocarbons, are separated off by condensation.

The gas phase taken off from the phase separation vessel (6) is compressed by means of the compressor (7) and recirculated to the hydroformylation reactor. The condensable constituents which have separated out in the phase separation vessel (6) are conveyed via the pressure pump (8) to the degassing column (9). The unreacted olefin is obtained at the top of the column (9) and is recirculated via line (14) to the hydroformylation reactor. At the bottom of the column (9), degassed hydroformylation product is taken off and part of this is passed to further work-up and part is cooled in the heat exchanger (10) and serves as scrubbing liquid for scrubbing the waste gas stream taken from the hydroformylation reactor (1) via line (11) in the scrubbing column (12). The waste gas obtained at the top of the column (12) is discharged from the system. The scrubbing liquid laden with unreacted olefin obtained at the bottom of the column (12) is conveyed via line (13) to the degassing column (9).

Figure 3:
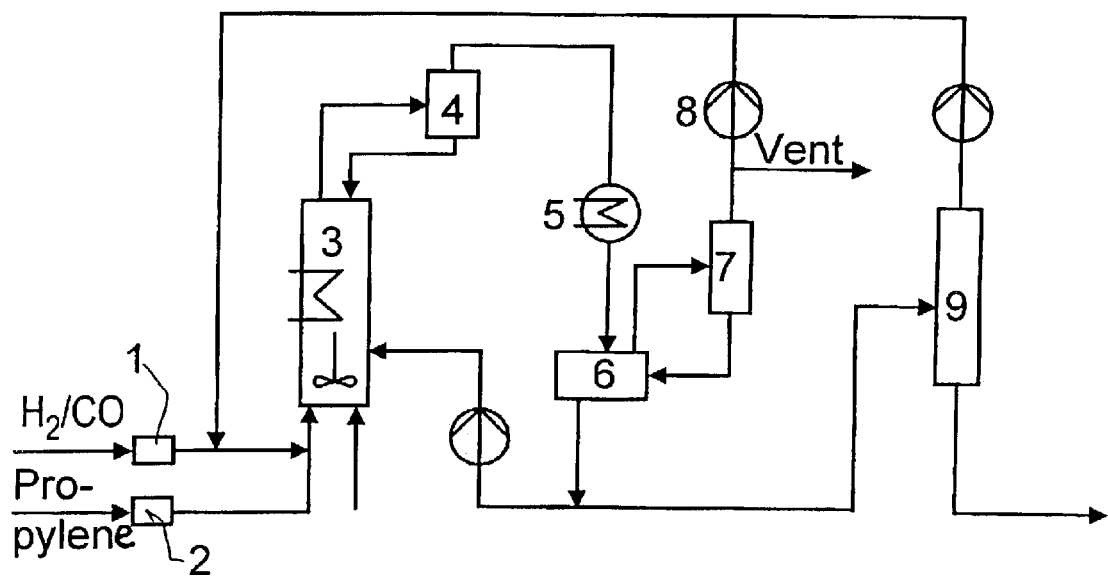

FIG. 3 schematically shows a plant of the prior art without scrubbing of the bleed stream (vent).

The invention is illustrated by the following example.

EXAMPLE

A plant as shown in FIG. 1 is used. A feed stream of 10 t/h of 95%-pure propylene (remainder: propane), a recycle stream of 3.2 t/h from the rectification column (6) and the synthesis gas necessary for the reaction were fed to the reactor. The hydroformylation products (n-butyraldehyde and isobutyraldehyde) together with the unreacted propylene and the propane introduced and formed in the reaction were carried from the reactor by means of a circulating gas stream. The condensable components were condensed out in the downstream condenser (2) and collected in the subsequent separator (3). The liquid phase comprised 78.3% by weight of butyraldehyde, 14.3% by weight of propylene and 7.4% by weight of propane. This liquid phase was fed (20.3 t/h) to the degassing column (5) where it was separated into a crude oxo product which is free of $C_3$-hydrocarbons and is obtained at the bottom (15.9 t/h) and a mixture of 66% of propylene and 34% of propane which is obtained at the top of the column (4.4 t/h). The propylene/propane mixture is fractionated in the column (6) to give a virtually propylene-free propane stream at the bottom (1.2 t/h) and a mixture of 90% of propylene and 10% of propane at the top (3.2 t/h). This stream was fed back to the propylene feed to the reactor (1). A substream (6.5 t/h) (9) was taken off from the circulating gas system and fed to the column (10). The circulating gas stream has the following composition:

51% by weight of propane
32% by weight of propylene
4% by weight of $H_2$
4% by weight of CO
3% by weight of butyraldehyde
3% by weight of $N_2$
1% by weight of methane 19 t/h of butyraldehyde at 35° C. from the bottom of the degassing column (5) were introduced into the upper part of the column (10). The degassing column was provided with four beds of packing. The heat of absorption was removed via two external heat exchangers and the temperature was maintained at 35° C. The valuable propylene, propane and a large part of the butyraldehyde present in the bleed stream were scrubbed out and returned together with the bottoms to the degassing column (5) (24.5 t/h). The recirculated mixture had the following composition: 78% by eight of butyraldehyde, 14% by weight of propylene, 8% by weight of propane.

The waste gas (0.9 t/h) discharged from the system had the following composition:

28% by weight of $H_2$
36% by weight of CO
26% by weight of $N_2$
6% by weight of $CH_4$
0.5% by weight of propylene
0.03% by weight of propane
3% by weight of butyraldehyde It can be seen that the unreacted propylene present in the bleed stream can mostly be returned to the process by means of the scrubbing according to the present invention of the bleed stream.

We claim:

1. A process for the hydroformylation of olefins having from 2 to 8 carbon atoms, in which
   a) an olefin-containing feed and a gas mixture comprising hydrogen and carbon monoxide are fed into a reaction zone and reacted in the presence of a hydroformylation catalyst,
   b) the crude hydroformylation product is separated from the output stream from the reaction stream from the reaction zone, a gaseous bleed stream is discharged and the remainder of the output stream is recirculated to the reaction zone, wherein
   c) the bleed stream is brought into intimate contact with a scrubbing liquid to remove unreached olefins present in the bleed stream, where the scrubbing liquid is degassed hydroformylation product, and the olefin-laden scrubbing liquid together with the crude hydroformylation product is passed to work-up.

2. A process as claimed in claim 1, wherein the bleed stream and the scrubbing liquid are brought into contact in a column in which the bleed stream is introduced into the bottom or the lower part of the column and the scrubbing liquid is introduced at the top or in the upper part of the column and is passed through the column in countercurrent to the bleed stream.

3. A process as claimed in claim 1, wherein the gas mixture comprising carbon monoxide and hydrogen contains from 1 to 15% by volume of inert gases.

4. A process as claimed in claim 1, wherein the scrubbing liquid is cooled to below 50° C. before being brought into contact with the bleed stream.

5. A process as claimed in claim 2, wherein the column and/or the scrubbing liquid conveyed in countercurrent to the bleed stream are/is cooled.

6. A process as claimed in clam 1, wherein the olefin used is propylene and n-butanal and isobutanal are produced.

7. A process as claimed in claim 1, wherein the hydroformylation catalyst used is a phosphorus-containing rhodium catalyst.

8. A process as claimed in claim 1, wherein the bleed stream which has been treated with the scrubbing liquid is cooled and/or compressed until the hydroformylation product present therein condenses.

9. A process as claimed in claim 1, wherein the olefin partial pressure in the reaction zone is from 30 to 40% of the total pressure in the reaction zone.

10. A process as claimed in claim 1, wherein the bleed stream which has been treated with the scrubbing liquid is utilized to generate heat or is used as starting material for the preparation of methanol.

\* \* \* \* \*